(12) United States Patent  
Lockard

(10) Patent No.: US 9,993,848 B2  
(45) Date of Patent: Jun. 12, 2018

(54) KNIFE BLOCK SANITIZER GUARD

(71) Applicant: The Academy of Bacteriology, LLC, Boynton Beach, FL (US)

(72) Inventor: Kenneth G. Lockard, Boynton Beach, FL (US)

(73) Assignee: The Academy of Bacteriology, LLC, Boynton Beach, FL (US)

(*) Notice: Subject to any disclaimer, the term of this patent is extended or adjusted under 35 U.S.C. 154(b) by 299 days.

(21) Appl. No.: 14/699,150

(22) Filed: Apr. 29, 2015

(65) Prior Publication Data

US 2016/0214128 A1    Jul. 28, 2016

Related U.S. Application Data

(63) Continuation-in-part of application No. 14/606,174, filed on Jan. 27, 2015.

(51) Int. Cl.  
    *B08B 3/02*              (2006.01)  
    *B08B 9/00*              (2006.01)  
    (Continued)

(52) U.S. Cl.  
CPC .............. *B08B 3/026* (2013.01); *A47G 21/14* (2013.01); *B05B 1/044* (2013.01); *B05B 1/14* (2013.01); *B05B 15/16* (2018.02); *B08B 9/00* (2013.01); *A61L 2/22* (2013.01); *B05B 1/22* (2013.01); *B05B 1/28* (2013.01); *B05B 11/0029* (2013.01)

(58) Field of Classification Search  
CPC ....... B08B 3/026; B08B 9/00; B05B 11/0013; B05B 15/067; B05B 1/28; B05B 11/0005; B05B 1/00; B05B 1/14; B05B 1/22; B05B 1/26; B05B 1/262; B05B 1/265; B05B 1/267; B05B 15/04; B05B 15/16; B05B 1/044; B05B 1/04; B05B 15/00; B05B 15/14; B65D 50/00  
USPC ......... D23/213, 226, 227; 222/153.1, 153.13, 222/153.14  
See application file for complete search history.

(56) References Cited

U.S. PATENT DOCUMENTS 2,270,579 A * 1/1942 Chamberlin ............... A47L 1/02  
                                                 15/321  
4,373,753 A * 2/1983 Ayers .................... F16L 37/133  
                                                   285/319

(Continued)

FOREIGN PATENT DOCUMENTS

JP         59082964 A   *  5/1984   ............ B05B 7/005  
JP      2005288263 A   * 10/2005

OTHER PUBLICATIONS

Machine translation of JP 2005288263 A, dated Oct. 2005.*  
Machine translation of JP 59082964 A, dated May 1984.*

*Primary Examiner* — Joseph L. Perrin  
*Assistant Examiner* — Kevin G Lee  
(74) *Attorney, Agent, or Firm* — Fleit Gibbons Gutman Bongini Bianco PL; Jon A. Gibbons

(57) ABSTRACT

Disclosed is a novel nozzle adapter for a spray bottle. The nozzle adapter coupled to a nozzle of spray bottle to allow a fluid chemical composition of sanitizing fluid to be forcefully discharged through it into the small opening cut outs of a knife block. The nozzle adapter serves as a guard to enter the opening and protect a splash back from occurring when the user applies a sanitizing fluid spray solution by pressure into the inside portion of the knife block slots which are of various sizes.

7 Claims, 19 Drawing Sheets

(51) Int. Cl.
*A47G 21/14* (2006.01)
*B05B 1/04* (2006.01)
*B05B 1/14* (2006.01)
*B05B 1/28* (2006.01)
*B05B 1/22* (2006.01)
*A61L 2/22* (2006.01)
*B05B 11/00* (2006.01)

(56) References Cited

U.S. PATENT DOCUMENTS

| | | | | |
|---|---|---|---|---|
| 5,280,856 A | * | 1/1994 | Haggerty | B05B 1/005 239/288 |
| 5,833,675 A | * | 11/1998 | Garcia | A61M 3/0262 239/229 |
| 2002/0038826 A1 | * | 4/2002 | Hurray | B05B 12/002 239/600 |
| 2004/0149837 A1 | * | 8/2004 | Foster | B05B 1/12 239/333 |
| 2008/0296398 A1 | * | 12/2008 | Hickman | B01F 5/0428 239/8 |
| 2012/0330216 A1 | * | 12/2012 | Almohizea | A45D 34/04 604/20 |

* cited by examiner

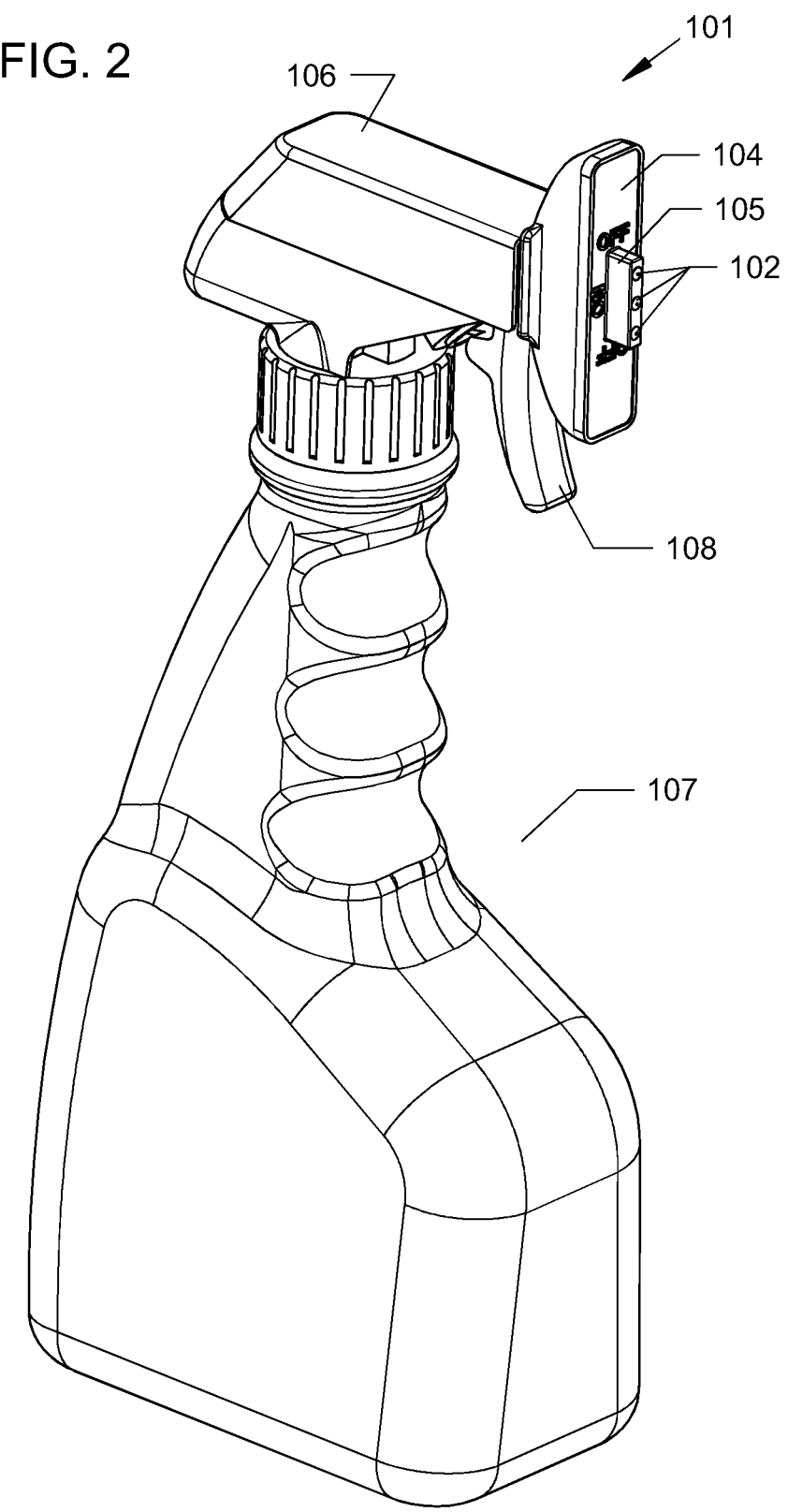

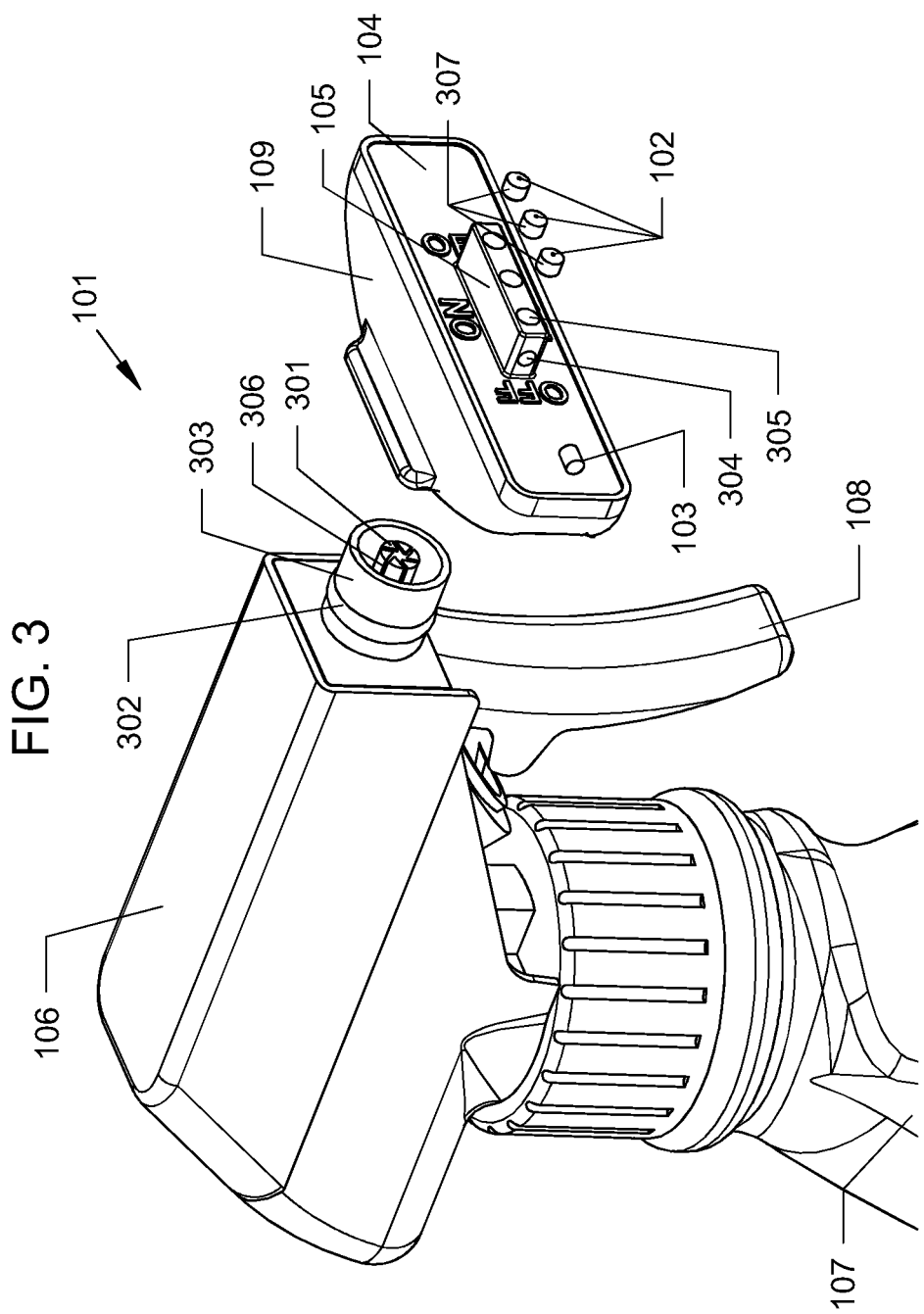

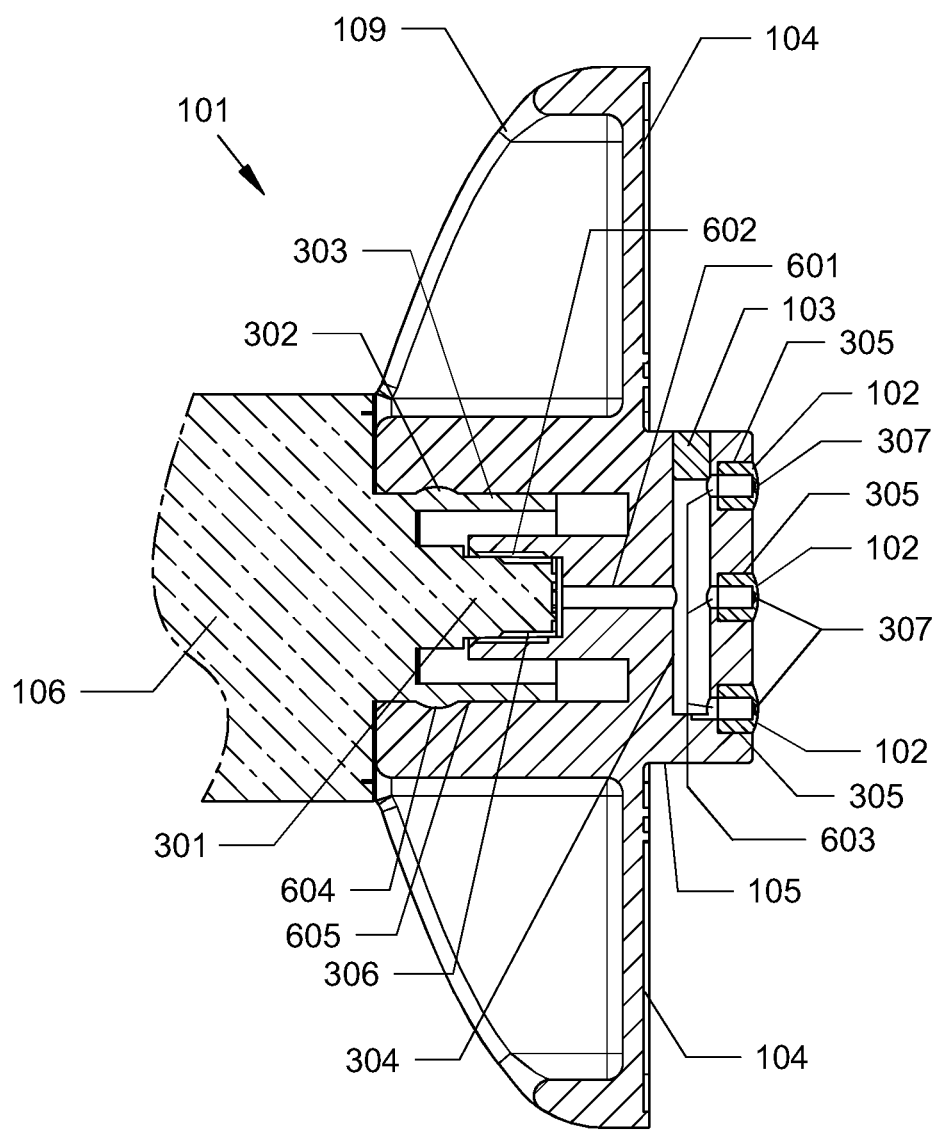

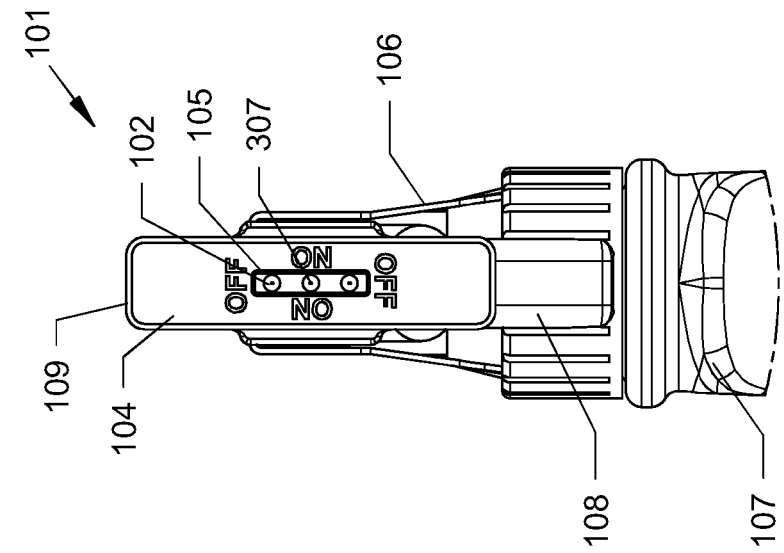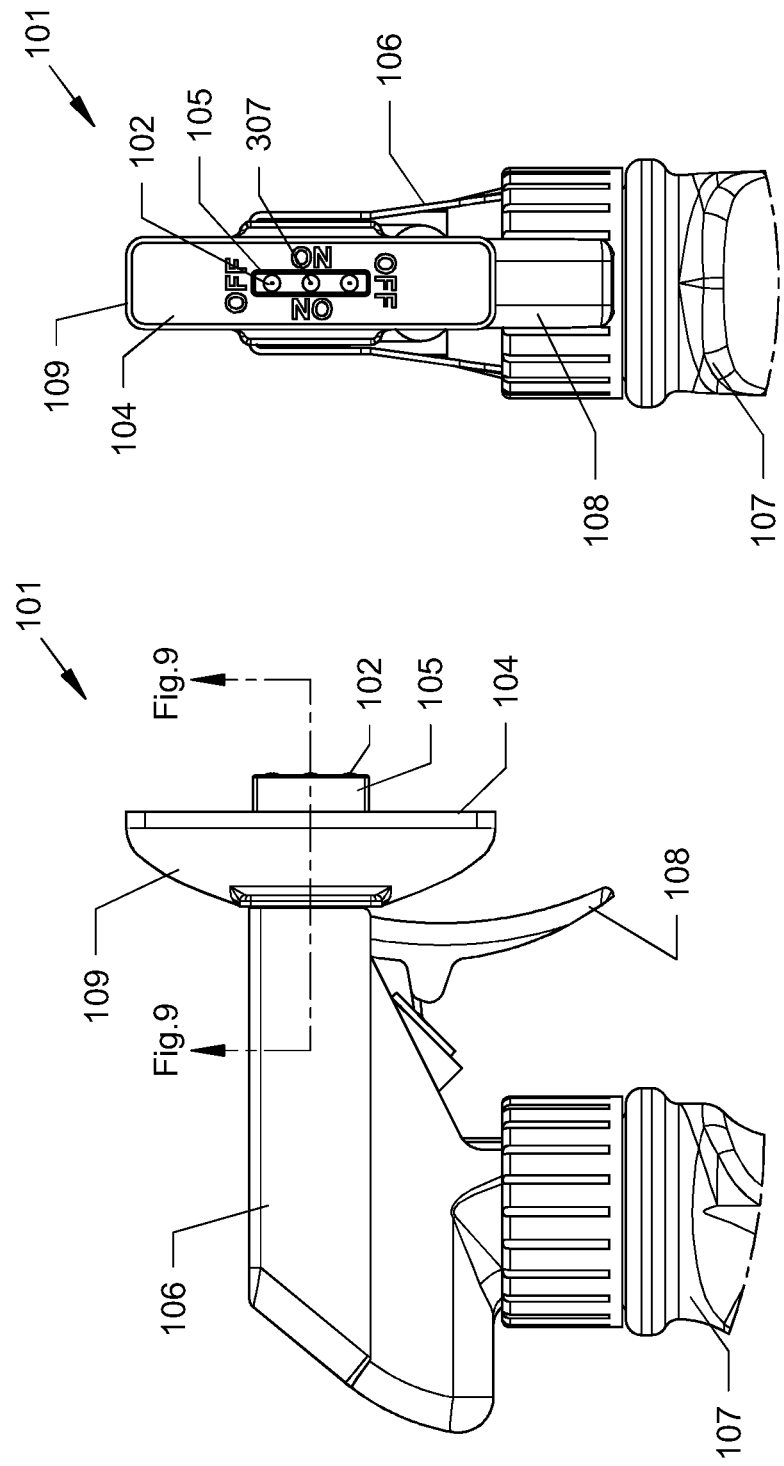

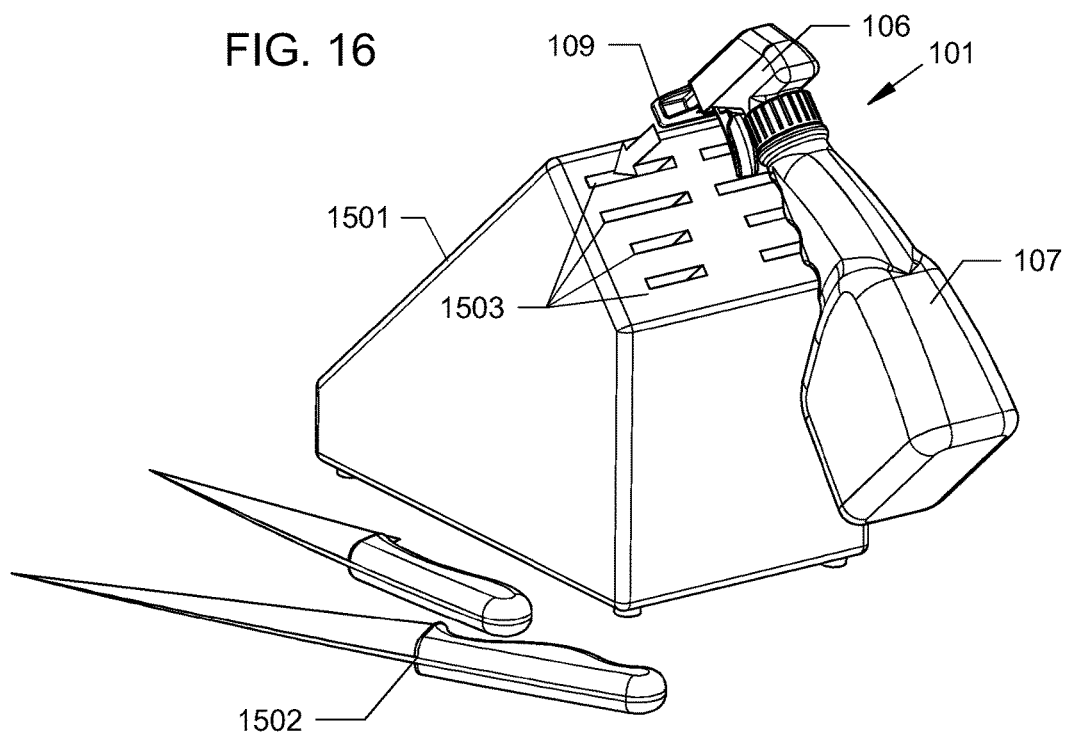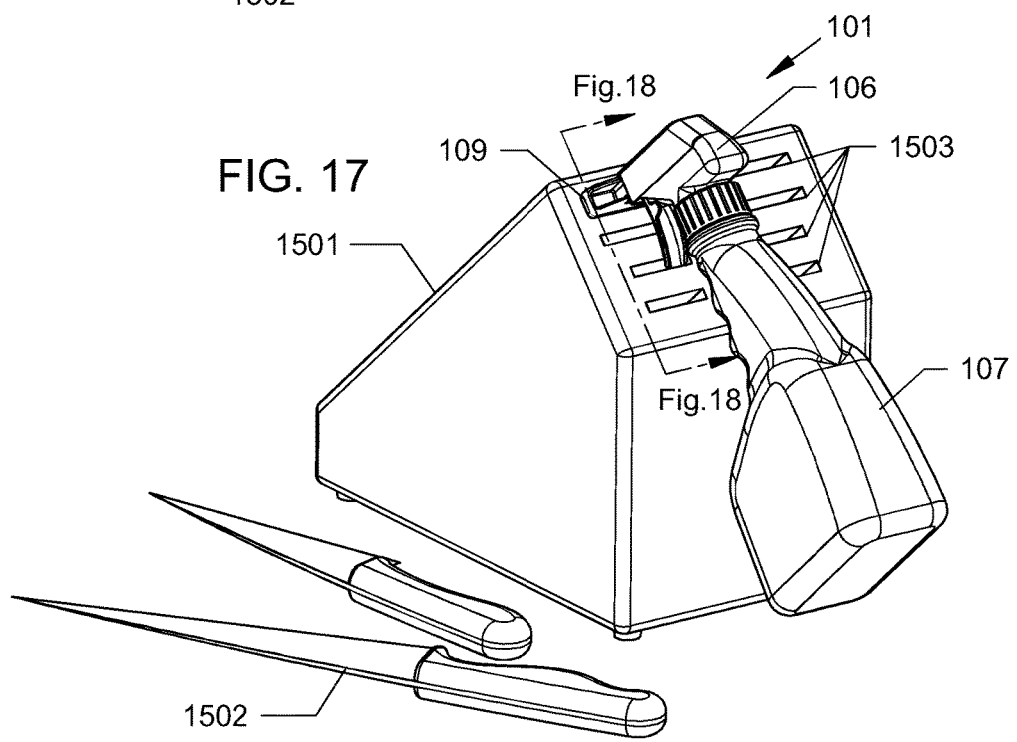

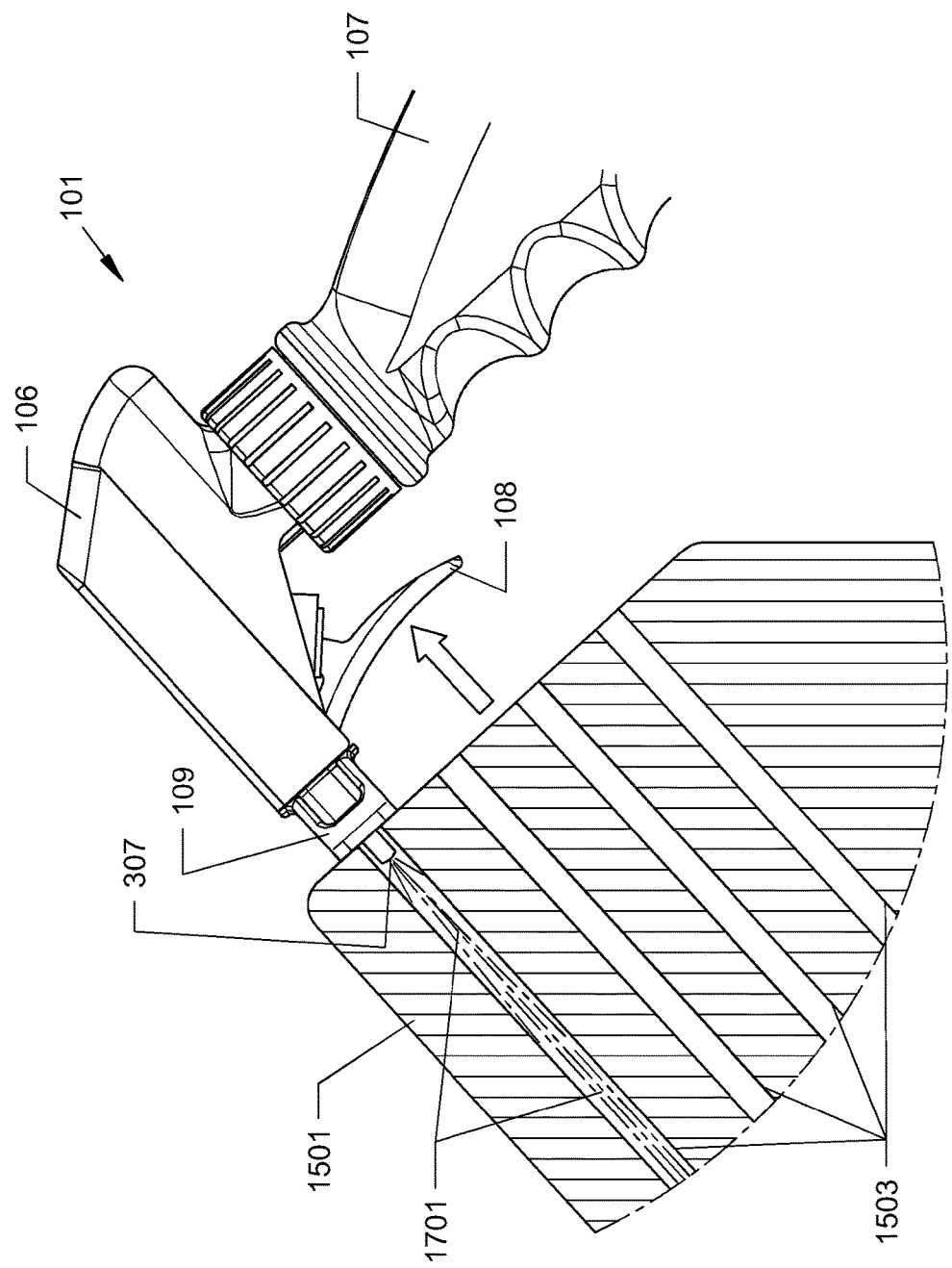

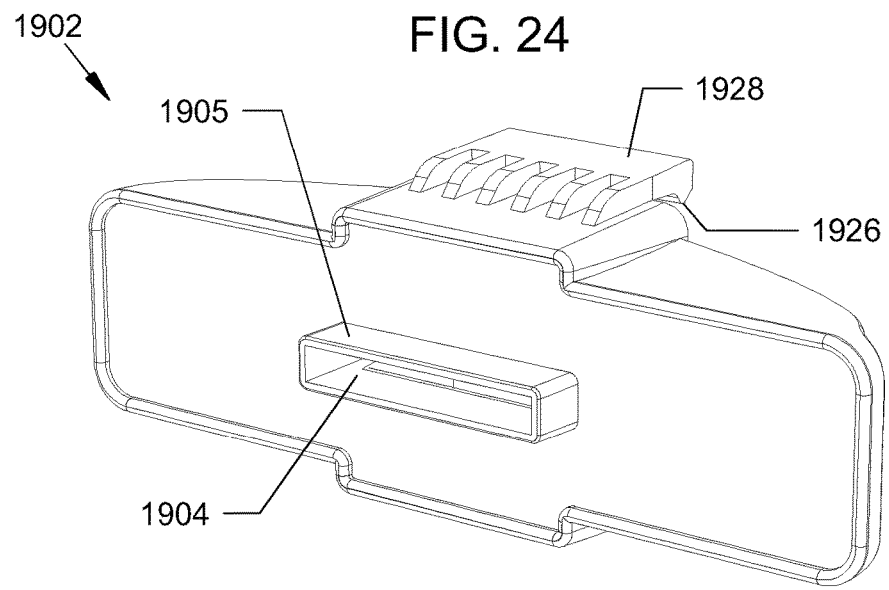
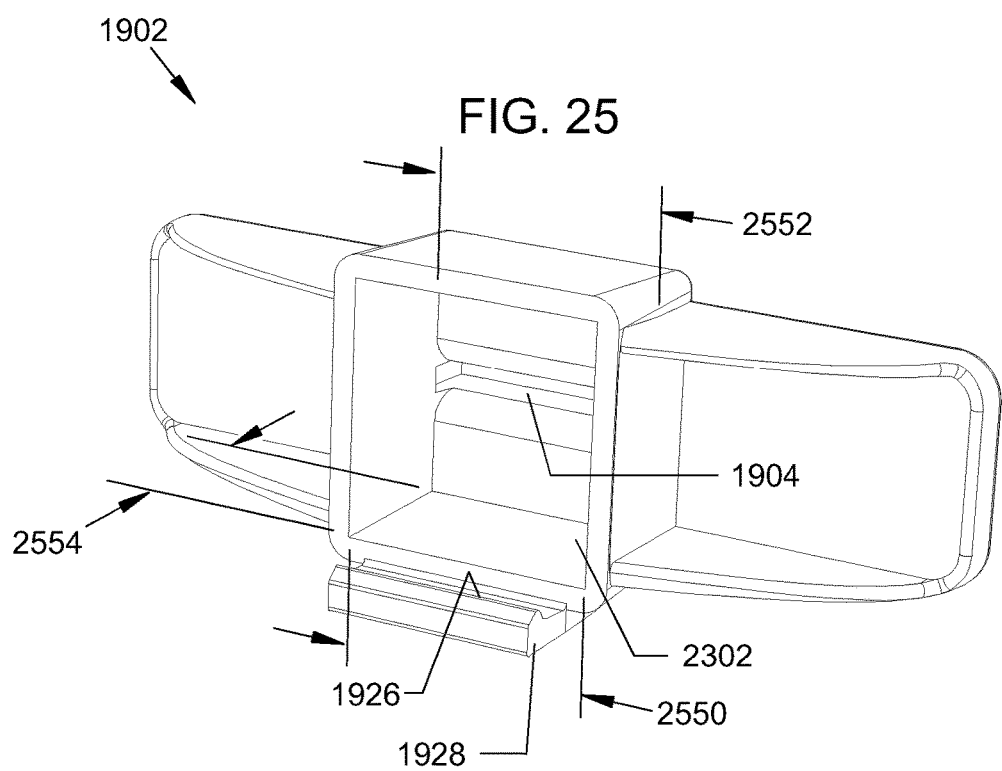

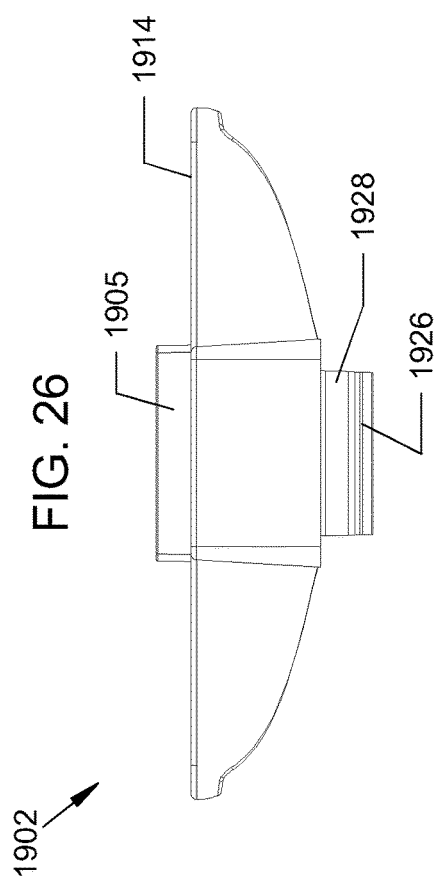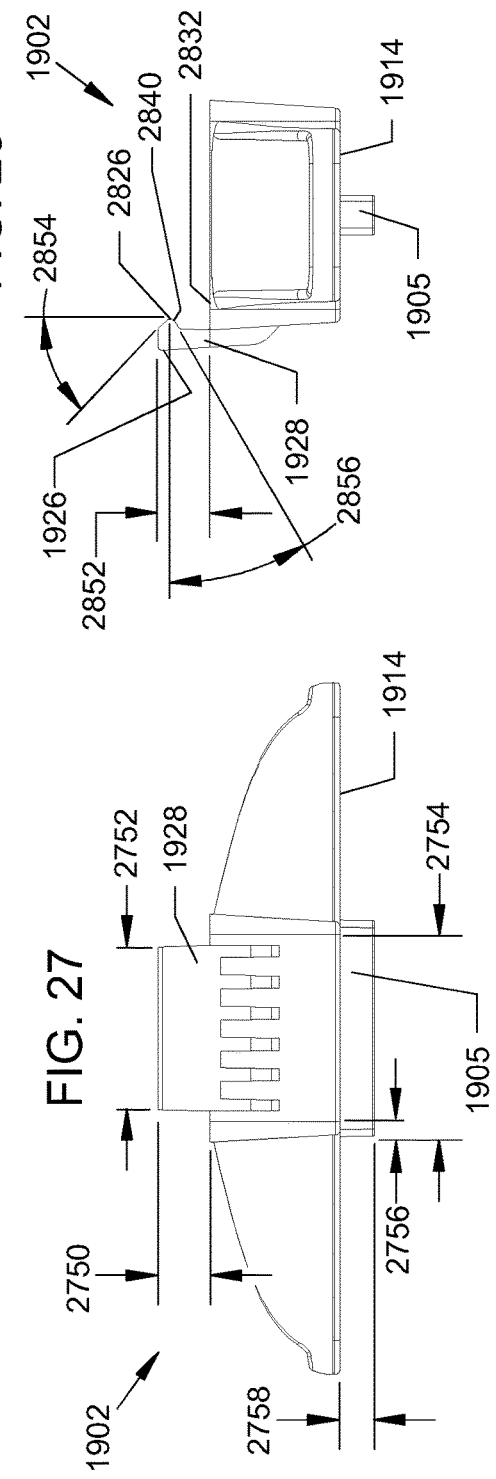

KNIFE BLOCK SANITIZER GUARD

CROSS-REFERENCE TO RELATED APPLICATIONS

The present invention is a continuation-in-part of U.S. patent application Ser. No. 14/606,174 filed, on Jan. 27, 2015 by Kenneth G. Lockard, and hereby incorporated by reference in its entirety.

BACKGROUND

The present invention generally relates to nozzles attached to spray bottles, and more specifically to a spray bottle attachment for sanitizing knife blocks.

SUMMARY

The presently claimed invention discloses a knife block spray sanitizer system for safely dispensing sanitizer fluid into the open slots of a knife block. The knife block spray sanitizer system uses an improved nozzle adapter for safely dispensing sanitizing fluid into the open slots of a knife block is described. The spray-attachment includes a rear intake side for working with commercially available pump heads that include an "on" and "off" rotatable outlet valve. The pump head provides pressurized sanitizing fluid that is sprayed out of the front discharge end. The front discharge end includes a substantially flat splash guard and a substantially rectangular slot guide disposed on the flat splash guard.

Disclosed is a novel nozzle adapter for a spray bottle. The nozzle adapter coupled to a nozzle of spray bottle allows a fluid chemical composition of sanitizing fluid to be forcefully discharged through it into the small opening cut outs of a knife block. The nozzle adapter serves as a guard to enter the opening and protect a splash back from occurring when the user applies a sanitizing fluid spray solution by pressure into the inside portion of the knife block slots which are of various sizes.

BRIEF DESCRIPTION OF THE SEVERAL VIEWS OF THE DRAWINGS

The accompanying figures wherein reference numerals refer to identical or functionally similar elements throughout the separate views, and which together with the detailed description below are incorporated in and form part of the specification, serve to further illustrate various embodiments and to explain various principles and advantages all in accordance with the present invention, in which:

FIG. 2. is a front perspective of knife block sanitizer assembly showing sanitizer head turned in an "off" position;

FIG. 3 is a front perspective detail of the pump head illustrating a first example of a sanitizer head removed with channel plug and sanitizer nozzles exploded from sanitizer head;

FIG. 6 is a top section detail of FIG. 4;

FIG. 7 is a side detail of sanitizer assembly with sanitizer head turned in an "off" position;

FIG. 8 is a front detail of FIG. 7;

FIG. 16 is a top perspective view of sanitizer assembly in position to be inserted into slot of knife block;

FIG. 17 is a top perspective view of sanitizer assembly inserted into slot of knife block;

FIG. 18 is a side section view of FIG. 17 showing the rectangular slot guide of the sanitizer head inserted into a slot of the knife block;

FIG. 24 is a Front perspective view of nozzle adapter (1902);

FIG. 25 is a rear perspective view of nozzle adapter (1902);

FIG. 26 is a bottom view of nozzle adapter (1902);

FIG. 27 is a top view of nozzle adapter (1902);

FIG. 28 is a side view of nozzle adapter (1902);

DETAILED DESCRIPTION

Figure 1:
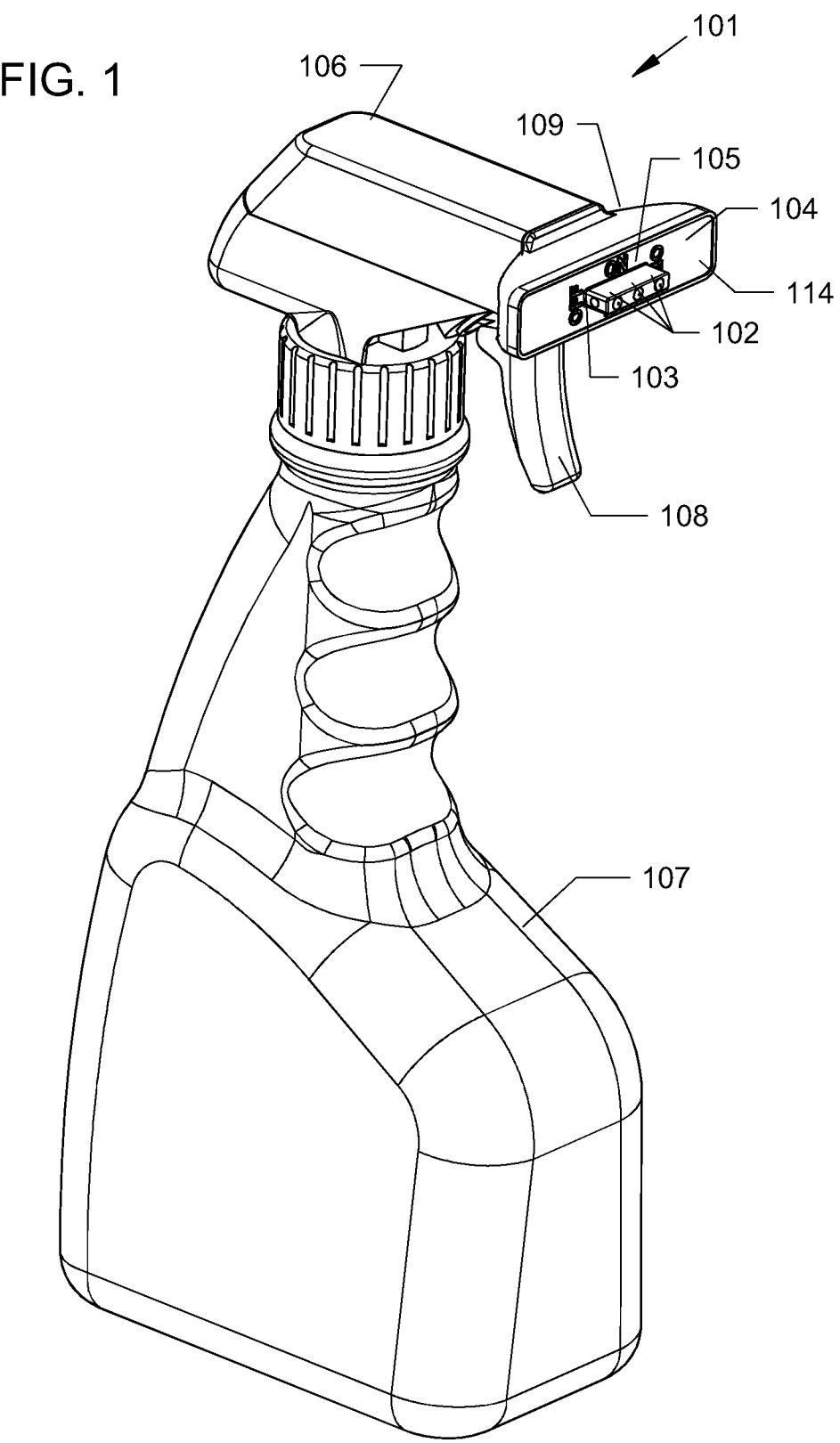
FIG. 1 is a front perspective of knife block sanitizer assembly showing sanitizer head turned in an "on" position.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The description of the presently claimed invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Overview

A "knife block" is a block of solid material, typically wood or plastic containing long grooves in which kitchen knives of various sizes can be inserted up to the handle. The slots are sized to accept a knife blade into it. Typically the slots are formed such that it is impossible to have access of the interior of the small slots openings. Contaminants are easily transmitted by knives inserted into the slots that were perhaps previously used to cut raw foods that were not cleaned or sanitized properly before replacing them back to the knife block. Studies made in 2013 by the N.S.F. National Sanitizing Foundation which is a worldwide agency and approved by the U.S. Government proved the following. Among the top 20 kitchen work items containing dangerous bacteria, their studies proved that the knife block was among the top three most dangerous items. Improperly washed knives returned to the knife block develop dangerous food born bacteria and germs in the dark moist and unattended environment of the small knife block slots. This, combined with the introduction of residue on the knives encourages this germ and bacteria growth that can bring about illness and even death. Therefore reducing and eliminating harmful germs, bacteria, and contaminants developing inside the slots of a knife block is a problem identified by the inventor.

Furthermore, the problem of achieving the sanitizing objective without a back splash or cover of some type when trying to spray liquids into these small multiple slots without a cover or guard of some type with today's large common spray tips has been identified as dangerous by the inventor.

Sanitizer Assembly

FIG. 1 is a front perspective of knife block sanitizer assembly (101) showing sanitizer head (109) turned in an "off" position. Shown is a bottle or fluid container (107) for holding sanitizing liquid. The fluid container is any material including metal, plastics, composites, or a combination thereof. A spray pump head (106) with a spray lever (108) is attached to the fluid container (107). In one example, the spray pump head (106) includes a suction tube not shown. One end of the suction tube is attached to the spray pump head (106) and the other end is inserted into the sanitizer liquid inside the fluid container (107). A spray-attachment (109) is mechanically coupled to the spray pump head (106). In other example, the spray-attachment (109) is mechanically attached to a fluid container which is pressurized (not shown), such as an aerosol can. The spray-attachment includes a substantially flat splash guard (104) that forms part of the front discharge side (114). A substantially rectangular slot guide (105) is disposed on the splash guard (104) as shown. The rectangular slot guide (105) is sized to fit inside into the slots (1503 of FIG. 18) of the knife block (1501 of FIG. 18) as shown in. 16-19. The rectangular slot guide (105) includes one or more nozzles (102) that distributes liquid into a spray over the slots (1503 of FIG. 18) of the knife block (1501 of FIG. 18).

In one example the sanitizer head (109) has two positions a first position "off" to prohibit spray to discharge and a second position "on" to allow spray to discharge. The first position or "off position" is shown in FIG. 1. FIG. 2 illustrates rotating the sanitizer head (109) approximately 90 degrees turns the sanitizer head (109) to a second position or "on position".

First Example of Sanitizer Head

FIG. 3 is a front perspective detail of the spray pump head (106) showing a first example of a sanitizer head (109) removed with channel plug (103) and sanitizer nozzles (102) exploded from sanitizer head (109). The spray pump head (106) includes a substantially cylindrical pump head attachment boss (303). A snap ring (302) on the outer surface of the pump head attachment boss (303) keeps the sanitizer head (109) firmly in place. Disposed inside the pump head boss (303) is a mixing post (301). The mixing post (301) cooperates a rear intake side (FIG. 11) of the sanitizer head (109) to form an "on" and "off" valve.

Figure 5:
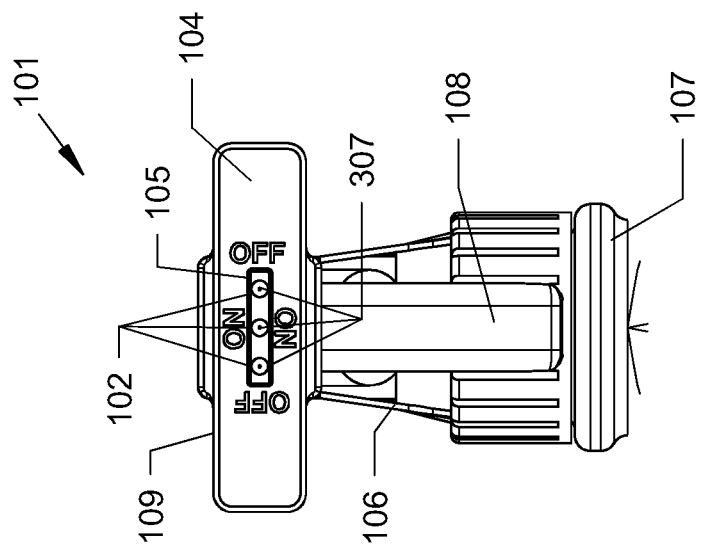
FIG. 5 is a front detail of FIG. 4.
Figure 4:
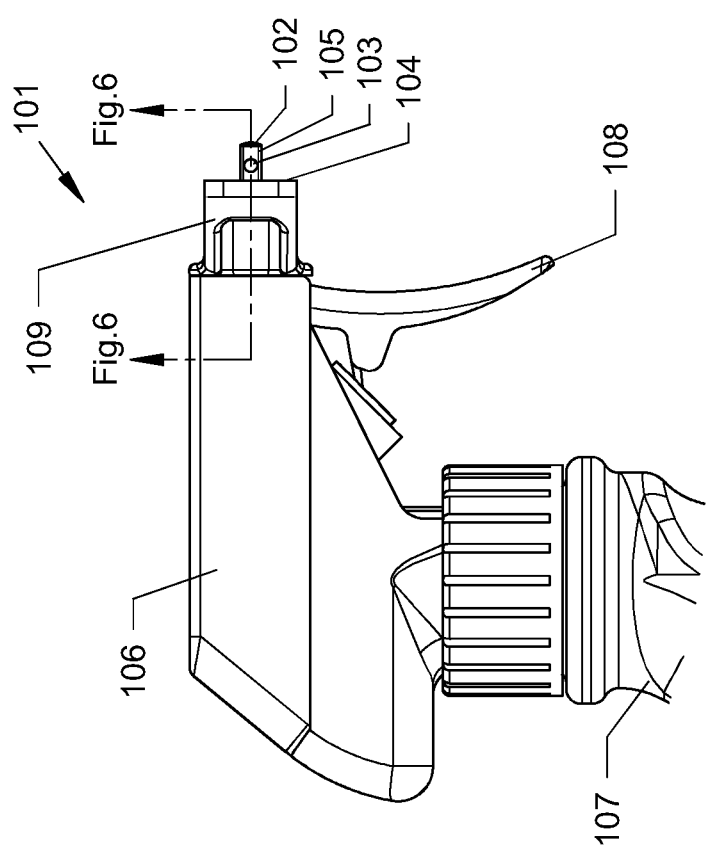
FIG. 4 is a side detail of sanitizer assembly with sanitizer head turned in an "on" position.
Figure 12:
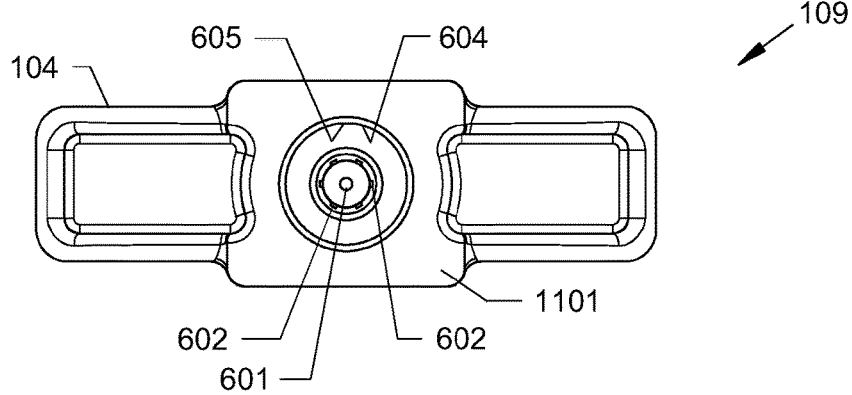
FIG. 12 is a rear view of sanitizer head.

FIG. 4 is a side detail of sanitizer assembly (101) with sanitizer head (109) turned in an "off" position and FIG. 5 is a front detail of FIG. 4. FIG. 6 is a top section detail of FIG. 4. Shown are the interior channels to allow sanitizer fluid to flow under pressure from the spray pump head (106) out through to sanitizer nozzles (102). The interior channels include a cylindrical head pass channel (602), a supply channel (601), and nozzle supply channel manifold (603) all providing a continuous fluid communication between the spray pump head (106) and sanitizer nozzles (102). As shown in FIG. 4 and FIG. 12 the cylindrical head pass channel (602) is disposed within the circular head attachment cavity (605). Further, the supply channel (601) is disposed within the cylindrical head (1102). Also shown is one or more ridges or snap ring (604) on the inner side wall (of the sanitizer head attachment cavity (605) that keeps the sanitizer head (109) firmly in attached. A series of head pass channels (602) are formed in the inner side wall (1116) of the cylindrical head (1102). The head pass channels in one position cooperate with the mixing post pass channels (306 of FIG. 3) of the mixing post (301) to create "on" and "off" valve.

Figure 9:
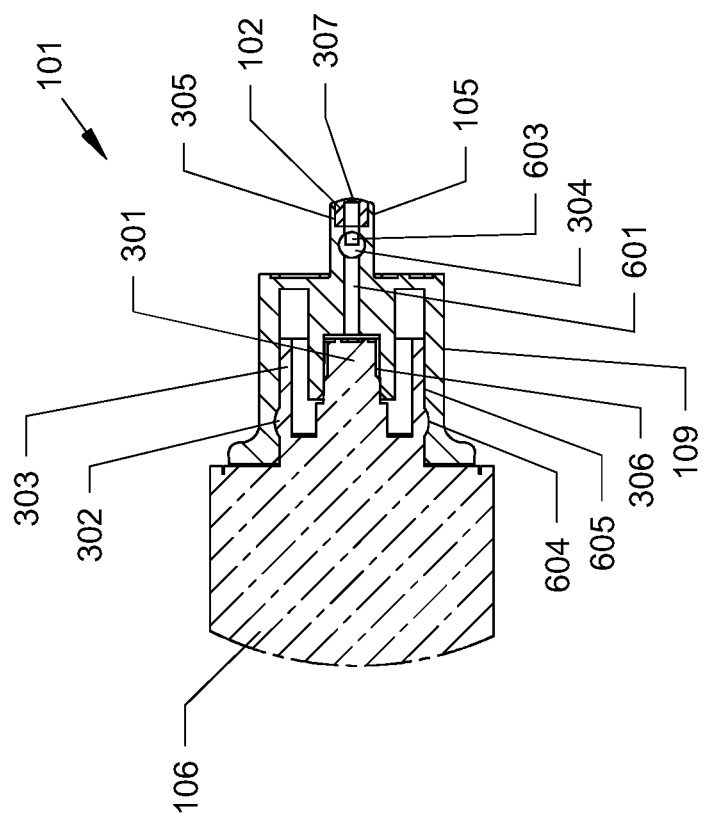
FIG. 9 is a top section detail of FIG. 7.
Figure 10:
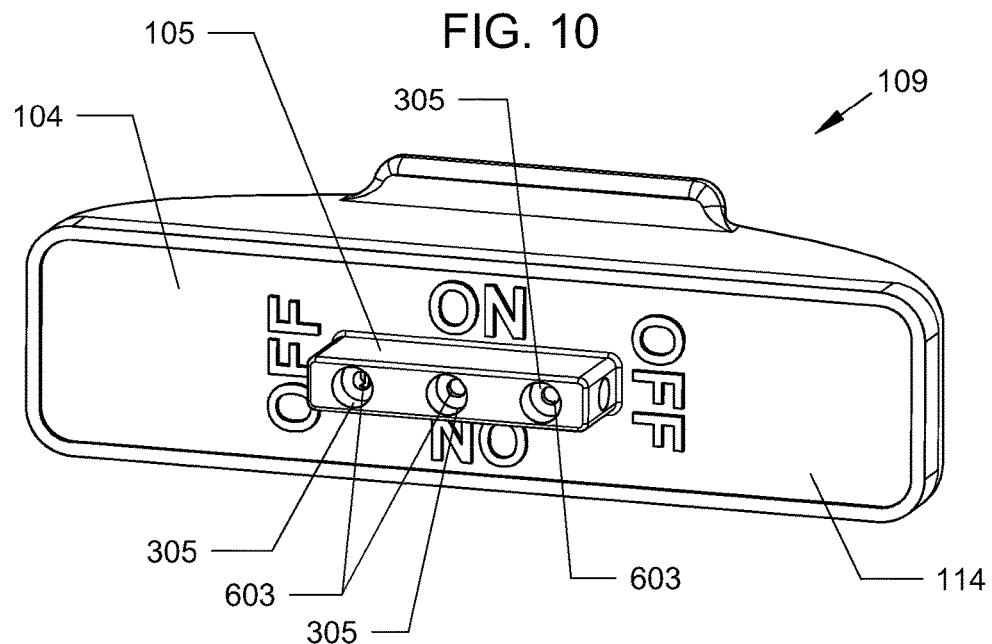
FIG. 10 is a front perspective view of sanitizer head.
Figure 11:
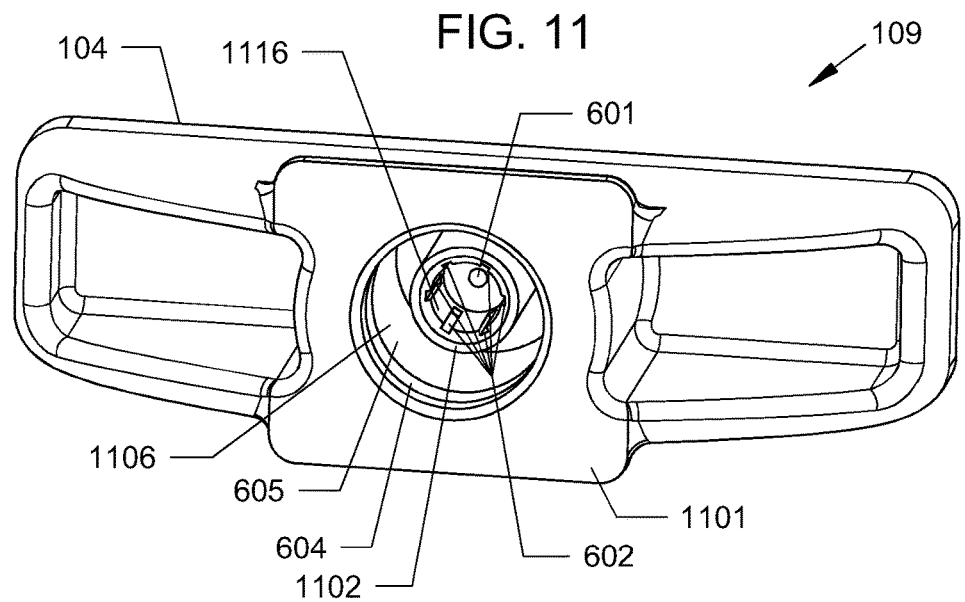
FIG. 11 is a rear perspective view of sanitizer head.
Figure 13:
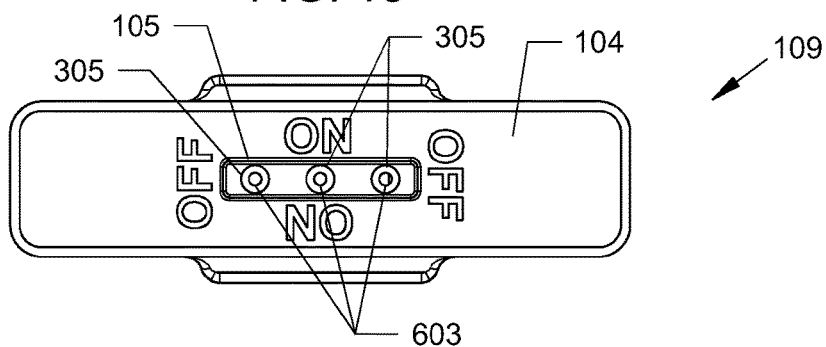
FIG. 13 is a front view of sanitizer head.
Figure 14:
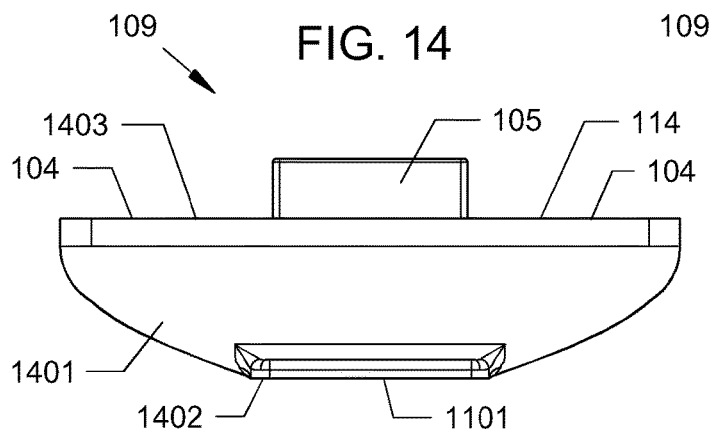
FIG. 14 is a top view of sanitizer head.
Figure 15:
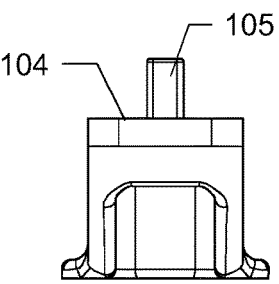
FIG. 15 is a side view of sanitizer head (109)

FIG. 7 is a side detail of sanitizer assembly (101) with sanitizer head (109) turned in an "off" position. FIG. 8 is a front detail of FIG. 7 and FIG. 9 is a top section detail of FIG. 7. FIG. 10 is a front perspective view of sanitizer head (109) and FIG. 13 is a front view illustrating of sanitizer head (109) a front discharge side (114). FIG. 11 is a rear perspective view of sanitizer head (109) and FIG. 12 is a rear view of sanitizer head (109) illustrating the rear intake side (1101). FIG. 14 is a top view of sanitizer head (109). In this example, the top view of the sanitizer head (109) is shaped substantially like an isosceles trapezoid (1401). The shorter edge (1402) of the isosceles trapezoid (1401) defining the rear intake side (1101) and the longer edge (1403) of the isosceles trapezoid (1401) defining the front discharge size (1403). FIG. 15 is a side view of sanitizer head (109).

FIG. 16 is a top perspective view of sanitizer assembly (101) in position to be inserted into slot (1503) of knife block (1501) and FIG. 17 is a top perspective view of sanitizer assembly (101) inserted into slot (1503) of knife block (1501).

FIG. 18 is a side section view of FIG. 17 showing the slot insert boss (105) of the sanitizer head (109) inserted into a slot (1503) of the knife block (1501). The nozzle spray orifices (307) can be seen spraying sanitizer fluid (1701) into the slot (1503).

In order to properly insert inside a slot of a knife block (1501), the rectangular slot guide (105) has a width approximately between 0.050 and 0.200 inches and in one example the width is approximately 0.100 inches. The length of the rectangular slot guide (105) is approximately between 0.200 and 0.800 inches and in one example the length is approximately 0.625 inches. The depth of the rectangular slot guide (105) is approximately between 0.100 and 0.400 inches and in one example the depth is 0.200 inches.

All fluids based upon or containing anti-bacterial compounds, anti-viral compounds, and/or anti-fungal compounds properties could be used in the device including but not limited to ones based on vinegar, alcohol, iodine, silver, silver nitrate, zinc, citric acid, hydrogen peroxide as well as combinations and compounds thereof.

Although a clear sanitizing fluid as used in one embodiment of the presently claimed invention, other types of sanitizing fluids and foams may be dispensed in various forms by the nozzle trigger including fluids, liquids, aerosols, sprays, streams and/or the like. In another example, a user is able to mix an inexpensive ½ teaspoon of bleach with a one or more cups of water.

Second Example of Sanitizer Head

Figure 19:
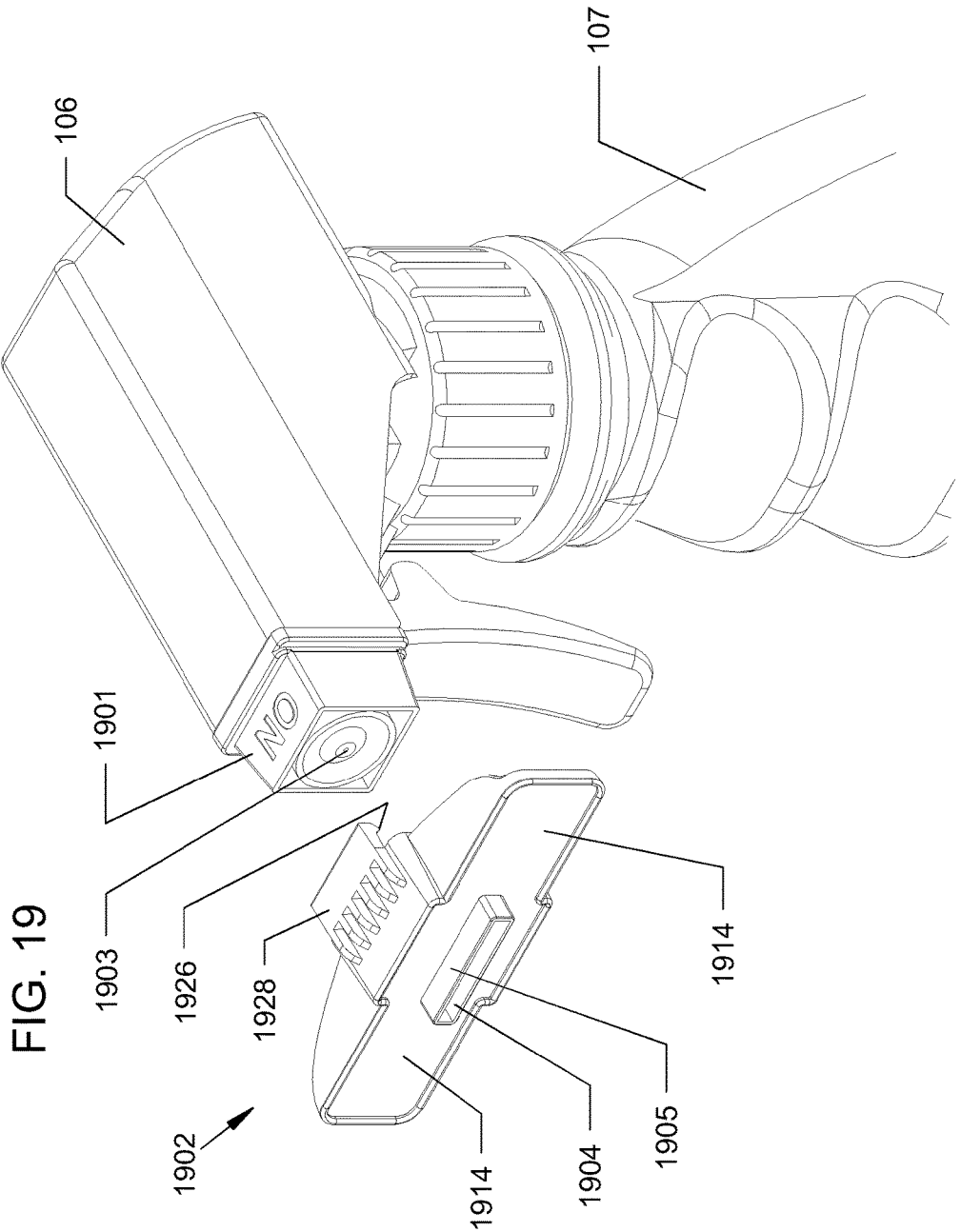
FIG. 19 is a top perspective view of a pump head illustrating a second example of a showing knife block spray nozzle adapter ready to be assembled.

FIG. 19 is a top perspective view of a pump head (106) illustrating a second example of a knife block spray nozzle adapter (1902) ready to be assembled. A spray nozzle office (1903) is formed within a spray nozzle (1901). An atomized spray may be ejected from the spray nozzle office (1903) on the splash guard (1914).

With reference to the knife block spray nozzle adapter (1902), illustrated is at least one friction arm (1928) with one or more friction finger contacts (1926). More specifically, the friction arm (1928) has a first end attached to the spray nozzle adapter as shown, and a second end with one or more friction finger contacts (1926) formed thereon. The friction finger contacts (1926) acts to apply a pressure to top of the spray nozzle (1901) when the knife block spray nozzle adapter (1902) is assembled to the spray nozzle (1901). The purpose of friction finger contacts (1926) is to keep the knife block spray nozzle adapter (1902) firmly attached to the spray nozzle (1901).

Figure 20:
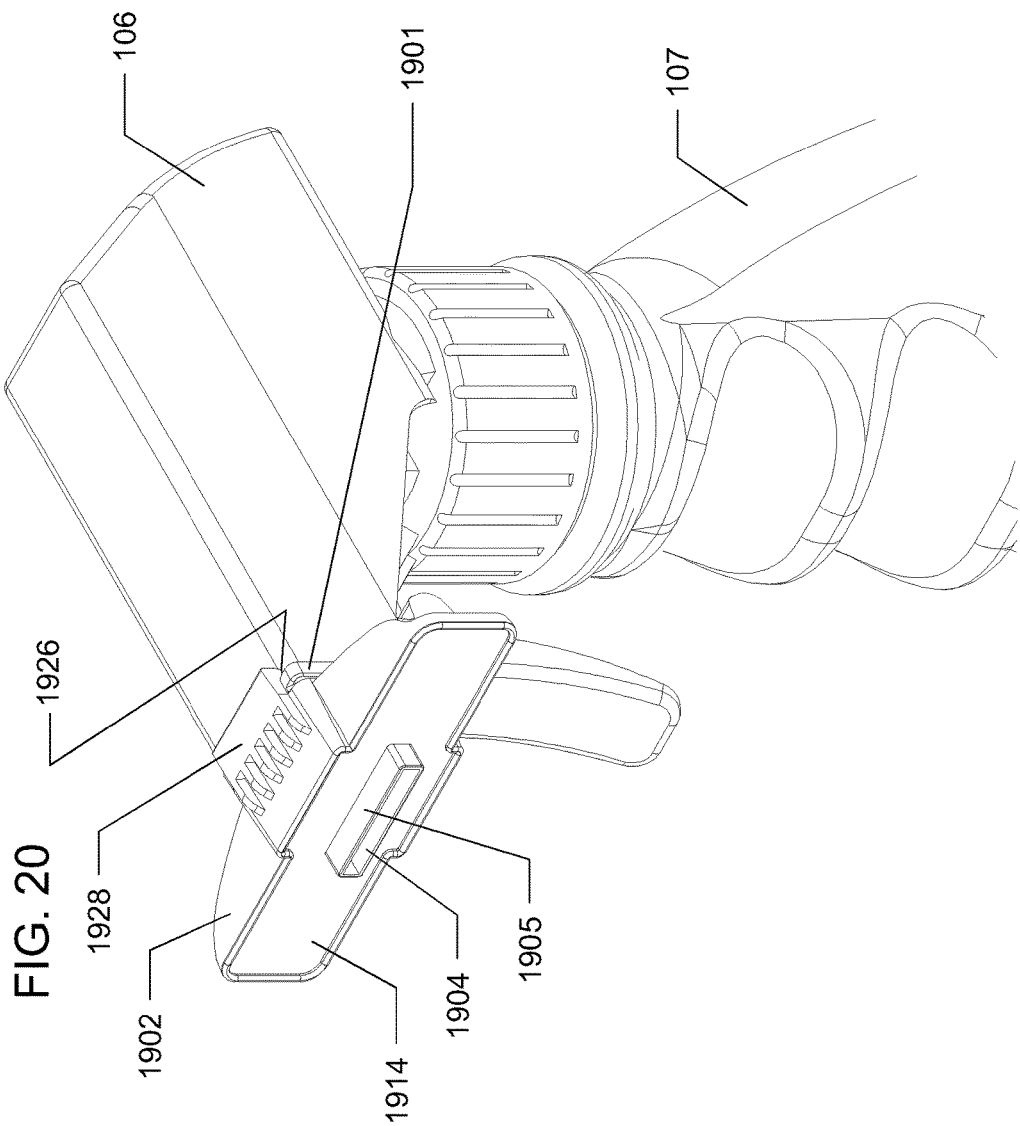
FIG. 20 is the spray nozzle adapter of FIG. 19 illustrating adapter assembled to pump head.
Figure 21:
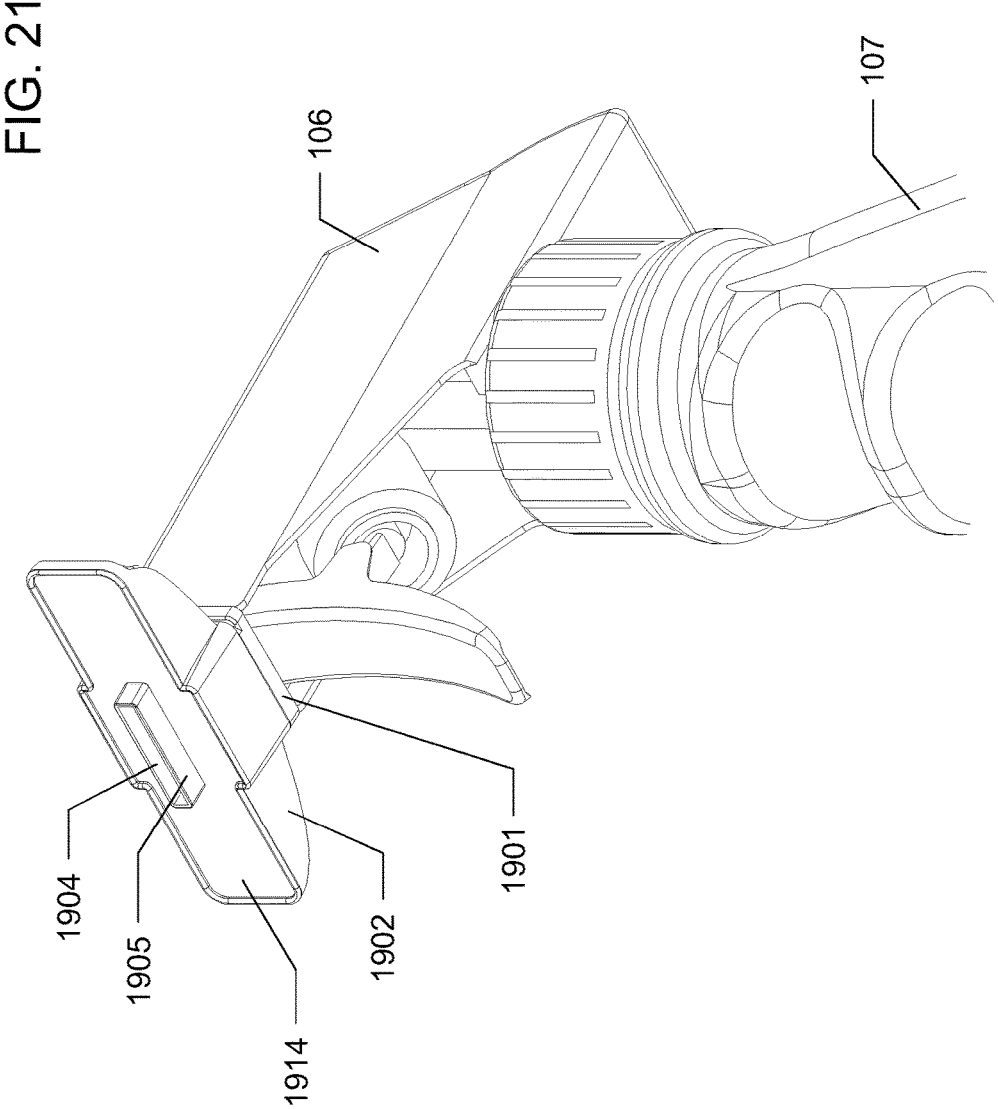
FIG. 21 is a bottom perspective view of FIG. 20.
Figure 22:
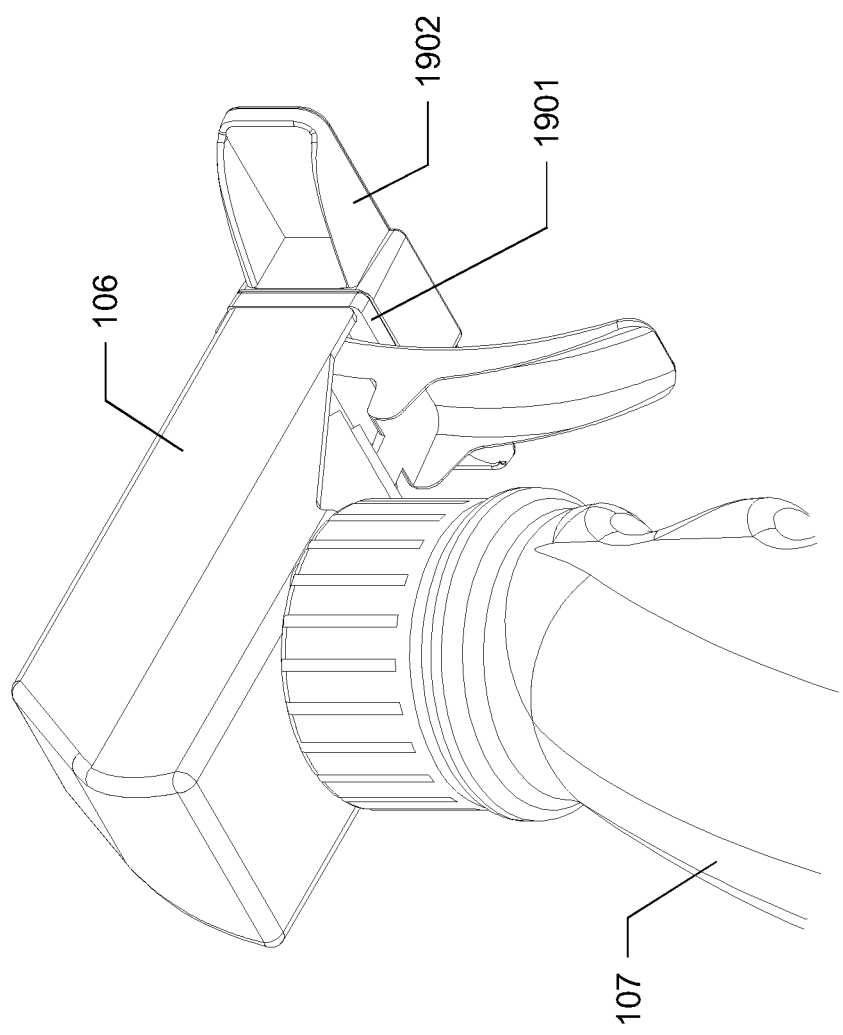
FIG. 22 is a bottom rear perspective view of FIG. 20.
Figure 23:
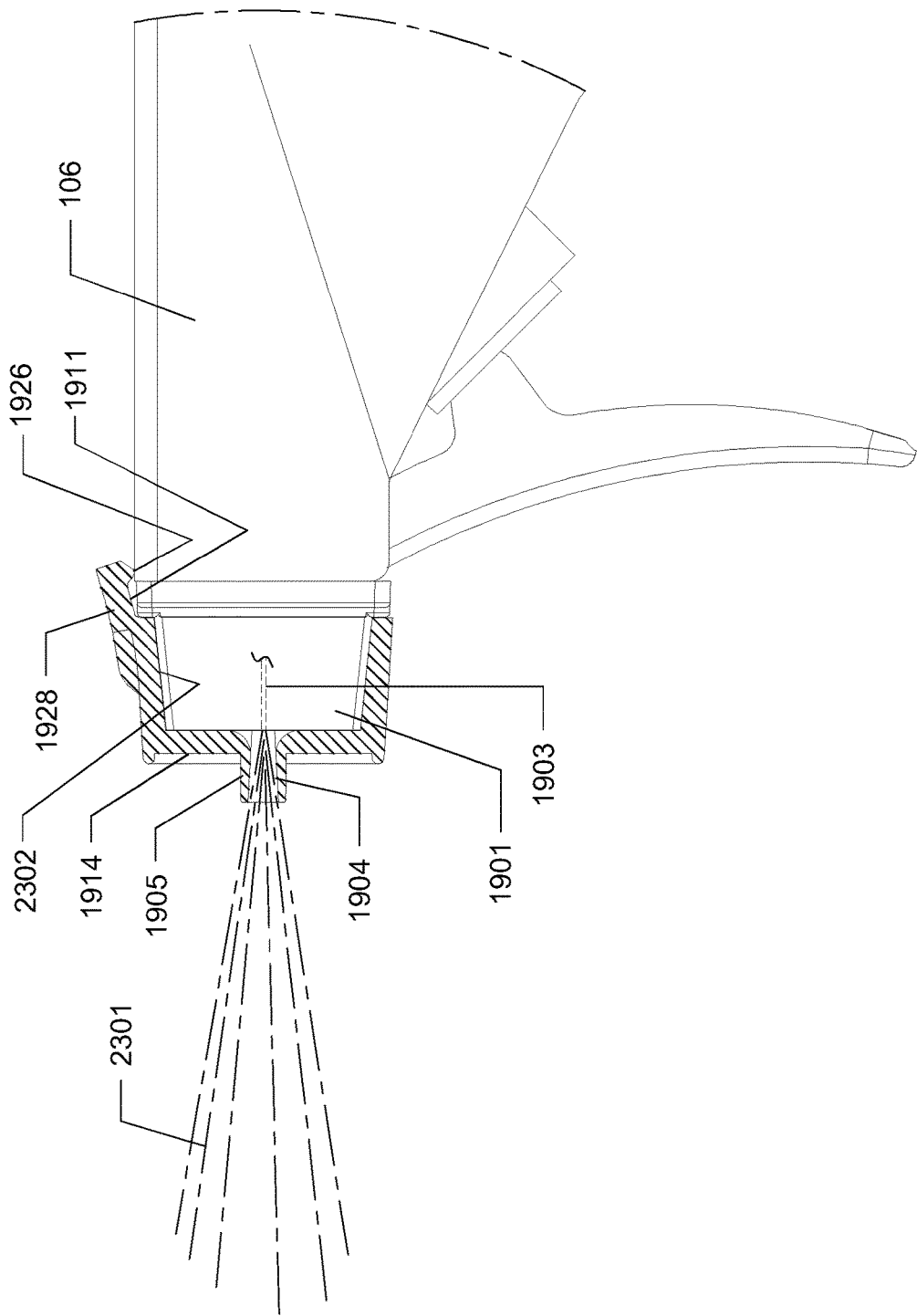
FIG. 23 is a side view of a pump head (106) with a sectioned nozzle adapter (1902) shown assembled.

The block spray nozzle adapter (1902) has a front discharge side (1914) with at least one substantially rectangular opening (1904) surrounded by a substantially rectangular slot insert boss (1905). FIG. 20 is the spray nozzle adapter of FIG. 19 illustrating adapter (1902) snapped-to the spray nozzle (1901) of the pump head (106). FIG. 21 is a bottom perspective view of FIG. 20 and FIG. 22 is a bottom rear perspective view of FIG. 20. FIG. 23 is a side view of a pump head (106) with a sectioned knife block nozzle adapter (1902) shown assembled. A sanitizer spray (2301) is shown being ejected from nozzle (1903) of pump head (106) through adapter (1902) out the rectangular opening (1904) surrounded by the slot insert boss (1905). The friction finger contacts (1926) extend over and are shown securely engaging or grabbing a lip (1911) formed in the spray nozzle (1901) of the pump head (106). The friction fingers contacts (1926) are flexible enough to permit repeated engaging and disengaging the lip (1911) when the knife block nozzle adapter (1902) is mounted and removed from the spray nozzle (1901).

FIG. 25 is a rear perspective view of nozzle adapter (1902). Shown is a substantially rectangular cavity (2302) formed within nozzle adapter (1902). The substantially rectangular cavity (2302) is formed and sized to accepts nozzle (106) being inserted into it and in fluid communication with the rectangular opening (1904). In one example, the rectangular cavity (2302) is approximately sized with a 0.561 inches square at the entry point (2550) and tapers down to 0.500 at the back (2552). The depth (2554) of the substantially rectangular cavity (2302) is approximately 0.292 inches. Other sizes are within the scope of the presently claimed invention. Also, although the substantially rectangular cavity (2302) is shown as substantially rectangular, other geometric shapes are possible, such as, round, oval, square, triangular and other polygons.

FIG. 26 is a bottom view of nozzle adapter (1902) and FIG. 27 is a top view of nozzle adapter (1902). The side view of a nozzle adapter (1902) is show in FIG. 28 illustrating details of friction finger contacts (1926). The friction finger contacts (1926) are approximately sized (2750) to extend 0.150 inches from the rear edge (2832) of the cavity (2302). The friction finger contacts (1926) contact point (2840) is substantially parallel to the rectangular cavity (2302) as shown. The friction finger contacts taper down slightly from 0.480 inches (2754) to 0.470 inches (2752) as shown. The rear cavity protrudes about 0.100 inches (2758) and slightly narrower by approximately 0.623 includes (2754) from each side of the rectangular cavity (2302) as shown.

Figure 29:
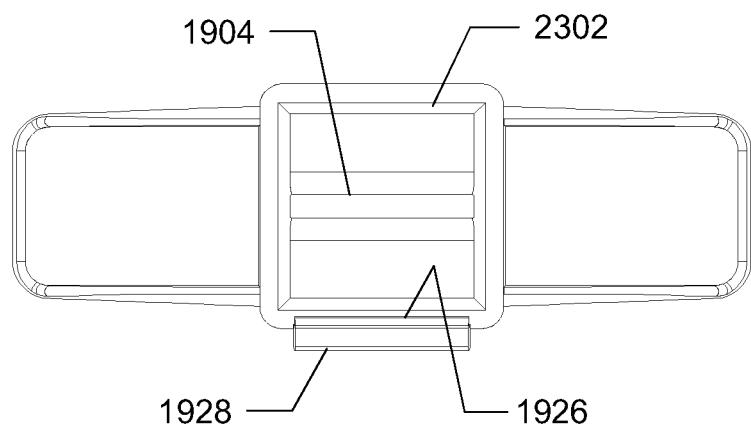
FIG. 29 is a rear view of nozzle adapter (1902)
Figure 30:
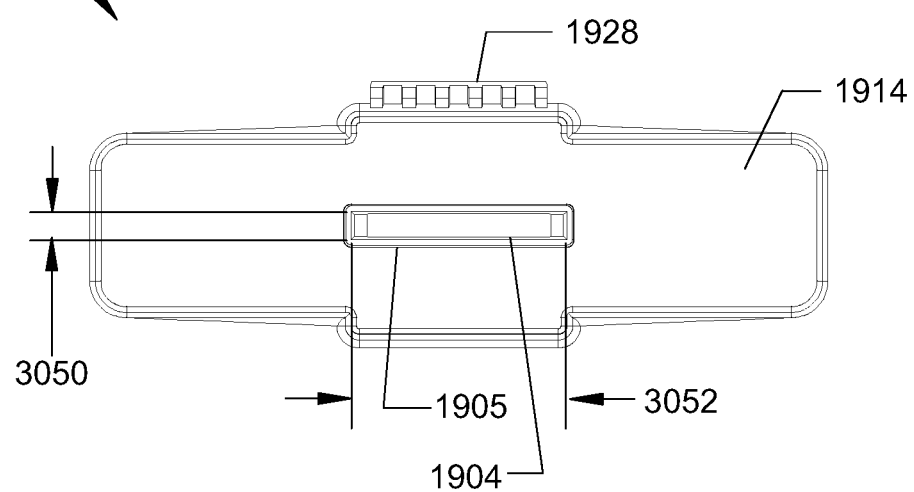
FIG. 30 is a front view of nozzle adapter (1902).

Also, an approximate angle of 40 degrees (2854) and 24 degrees (2856) is used to form the tip of finger (2826) as shown. Referring to FIG. 29 is a rear view of nozzle adapter (1902) showing the rear intake side. FIG. 30 is a front view of nozzle adapter (1902) showing front discharge size. The rectangular opening (1904) is approximately 0.078 inches in height (3050) and 0.585 inches in width (3052) surrounded by the slot insert boss (1905).

Further, although the presently claim invention is directed to decontamination and sanitizing knife blocks, other kitchen products, especially kitchen products with porous surfaces have been shown to be successfully decontaminated and sanitized. Kitchen products with porous surfaces, such as wood, are particularly difficult to properly clean. Using the currently claim invention, kitchen products with porous surfaces are including cutting boards, spoon rests, utensils, and bowls are decontaminated and sanitized as well.

Non-Limiting Examples

The terminology used herein is for the purpose of describing particular examples only and is not intended to be limiting of the invention. As used herein, the singular forms "a", "an" and "the" are intended to include the plural forms as well, unless the context clearly indicates otherwise. The term another, as used herein, is defined as at least a second or more. The terms "including" and "having" as used herein, are defined as comprising (i.e. open language). The term "coupled" as used herein, is defined as "connected" although not necessarily directly.

The description of the present application has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:
1. A knife block spray sanitizer system comprising:
   a fluid container;
   a pump head with a spray lever, mechanically attachable to the fluid container, the pump head including a rotatable spray nozzle with a substantially flat back surface with a raised lip mounted on a pump head attachment boss with a mixing post for discharging a pressurized fluid therefrom;
   an aftermarket removable nozzle adapter formed to be removably attached to the raised lip of the rotatable spray nozzle having a portion defined by a gap between the substantially flat back surface of the raised lip of the rotatable spray nozzle and the pump head, the raised lip on the substantially flat back surface flush around an entire perimeter, the aftermarket removable nozzle adapter with a front discharge side and a rear intake side,
   the rear intake side including a rectangular cavity for receiving a pressurized fluid;
   the front discharge side with a substantially flat splash guard and a substantially rectangular slot guide disposed thereon, the substantially rectangular slot guide protrudes from the substantially flat splash guard beyond the substantially flat splash guard, the substantially rectangular slot guide including at least one rectangular slot opening in fluid communica- tions with the rectangular cavity for directing the pressurized fluid therefrom; and a friction arm disposed only on a single side of the rectangular cavity and formed to protrude beyond the rectangular cavity with a first end attached to an outer surface of the rear intake side of the aftermarket removable nozzle adapter and a second end with one or more flexible friction finger contacts formed thereon for extending over and engaging with the raised lip of the rotatable spray nozzle, where the flexible friction finger contacts are formed with an angular tip engaging and disengaging with the raised lip and the gap when the aftermarket removable nozzle adapter is mounted and removed from the rotatable spray nozzle.

2. The knife block spray sanitizer system of claim 1, wherein the substantially rectangular slot guide has a width between 0.050 and 0.200 inches and a length between 0.200 and 0.800 inches.

3. The knife block spray sanitizer system of claim 2, wherein the substantially rectangular slot guide protrudes from the substantially flat splash guard between 0.100 inches and 0.400 inches.

4. The knife block spray sanitizer system of claim 1, wherein the friction arm extends approximately 0.150 inches from the rear intake side.

5. The knife block spray sanitizer system of claim 4, wherein the one or more friction finger contacts have a point formed to point substantially parallel to the rectangular slot opening.

6. The knife block spray sanitizer system of claim 1, wherein the aftermarket removable nozzle adapter is substantially shaped as an isosceles trapezoid with a shorter edge defining the rear intake side and a longer edge defining the front discharge side, and the substantially rectangular slot guide disposed on along the longer edge.

7. The knife block spray sanitizer system of claim 1, wherein the pressurized fluid includes at least one of anti-bacterial compounds, anti-viral compounds, anti-fungal compounds, or a combination thereof.

* * * * *